US006944330B2

(12) United States Patent
Novak et al.

(10) Patent No.: US 6,944,330 B2
(45) Date of Patent: Sep. 13, 2005

(54) INTERACTIVE COMPUTER-AIDED DIAGNOSIS METHOD AND SYSTEM FOR ASSISTING DIAGNOSIS OF LUNG NODULES IN DIGITAL VOLUMETRIC MEDICAL IMAGES

(75) Inventors: Carol L. Novak, Newtown, PA (US); Li Fan, Plainsboro, NJ (US); Jianzhong Qian, Princeton Junction, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 671 days.

(21) Appl. No.: 09/840,267

(22) Filed: Apr. 23, 2001

(65) Prior Publication Data

US 2002/0028006 A1 Mar. 7, 2002

Related U.S. Application Data

(60) Provisional application No. 60/230,772, filed on Sep. 7, 2000.

(51) Int. Cl.[7] ............................................. G06K 9/00
(52) U.S. Cl. ........................ 382/162; 382/128; 382/131; 382/132
(58) Field of Search ............................ 882/162, 128, 882/131, 132

(56) References Cited

U.S. PATENT DOCUMENTS

| 4,907,156 | A | | 3/1990 | Doi et al. .................... 364/413 |
|---|---|---|---|---|
| 5,459,536 | A | | 10/1995 | Shalon et al. ............... 351/226 |
| 5,491,627 | A | | 2/1996 | Zhang et al. ............ 364/413.2 |
| 5,579,360 | A | | 11/1996 | Abdel-Mottaleb ........... 378/37 |
| 5,699,082 | A | | 12/1997 | Marks et al. ................ 345/157 |
| 5,768,406 | A | | 6/1998 | Abdel-Mottaleb .......... 382/132 |
| 5,815,591 | A | | 9/1998 | Rochrig et al. ............. 382/130 |
| 5,838,815 | A | | 11/1998 | Gur et al. .................... 382/128 |
| 5,970,115 | A | | 10/1999 | Colbeth et al. ............... 378/62 |
| 5,970,164 | A | | 10/1999 | Bamberger et al. ......... 382/132 |
| 6,075,878 | A | | 6/2000 | Yoshida et al. ............. 382/132 |
| 6,119,033 | A | * | 9/2000 | Spigelman et al. ......... 600/426 |
| 6,246,782 | B1 | * | 6/2001 | Shapiro et al. ............. 382/128 |
| 6,556,696 | B1 | * | 4/2003 | Summers et al. ........... 382/128 |
| 6,630,937 | B2 | * | 10/2003 | Kallergi et al. ............. 345/619 |
| 2002/0006216 | A1 | * | 1/2002 | Armato et al. .............. 382/131 |

\* cited by examiner

*Primary Examiner*—Andrew W. Johns
*Assistant Examiner*—Patrick L. Edwards
(74) *Attorney, Agent, or Firm*—Donald B. Paschburg; F. Chau & Associates, LLC (57) ABSTRACT

A computer-assisted diagnosis method for assisting diagnosis of anatomical structures in a digital volumetric medical image of at least one lung includes identifying an anatomical structure of interest in the volumetric digital medical image. The anatomical structure of interest is automatically segmented, in real-time, in a predefined volume of interest (VOI). Quantitative measurements of the anatomical structure of interest are automatically computed, real-time. A result of the segmenting step and a result of the computing step are displayed, in real-time. A likelihood that the anatomical structure of interest corresponds to a disease or an area warranting further investigation is estimating, in real-time, based on predefined criteria and the quantitative measurements. A warning is generated, in real-time, when the likelihood is above a predefined threshold.

29 Claims, 6 Drawing Sheets

INTERACTIVE COMPUTER-AIDED DIAGNOSIS METHOD AND SYSTEM FOR ASSISTING DIAGNOSIS OF LUNG NODULES IN DIGITAL VOLUMETRIC MEDICAL IMAGES

CROSS-REFERENCE TO RELATED APPLICATIONS

This application claims the benefit of provisional application 60/230,772 filed on Sep. 7, 2000.

This application is related to U.S. patent application, Ser. No. 09/840,266, entitled "Method and System for Automatically Detecting Lung Nodules from High Resolution Computed Tomography (HRCT) Images", filed on Apr. 23, 2001, which is commonly herewith, and the disclosure of which is incorporated herein by reference. This application is also related to U.S. patent application Ser. No. 09/606,564, entitled "Computer-aided Diagnosis of Three Dimensional digital image data", filed on Jun. 29, 2000, and U.S. Pat. No. 6,697,506, entitled "Mark-Free Computer-Assisted Diagnosis Method and System for Assisting Diagnosis of Abnormalities in Digital Medical Images Using Diagnosis Based Image Enhancement", issued on Feb. 24, 2002, which are commonly assigned herewith, and the disclosures of which are incorporated herein by reference.

BACKGROUND

1. Technical Field

The present invention generally relates to computer-assisted diagnosis (CADx) and, in particular, to an interactive computer-aided diagnosis (ICAD) method and system for assisting diagnosis of lung nodules in digital volumetric medical images.

2. Background Description

Computer-Aided diagnosis (CADx) is an important technology in many clinical applications, such as the detection of lung cancer. In current clinical practice, cancer or other diseases may be missed during a physician's un-aided examination of medical image data, in part because of the large volume of data. This is particularly a problem for screening applications, since there is generally little time to devote to the examination of each patient's data, and the entire range of the data must be examined to make sure it is free from disease. Computer analysis that is performed silently in the background can greatly aid physicians in their work.

New technologies that offer three-dimensional (3-D) scans of the human body, such as Magnetic Resonance Imaging (MRI) and Computed Tomography (CT), offer tremendous opportunities for improved detection of disease. However the change from two dimensions to three, especially to large volume 3-D data (such as image volumes produced by multi-detector high resolution CT scanners), results in a much larger amount of data for the physician to examine. Furthermore, the low-dose imaging for cancer screening poses additional challenges to the traditional manual clinical reading. Thus, the assistance of computer analysis becomes even more important.

Unfortunately, many current CADx systems are not readily accepted by physicians, because their aid is seen as more of a distraction than a help. Many such systems present the results of the computer's diagnosis to the physicians by marks, such as a red circle or arrow on the softcopy, which some physicians believe can create a bias in their interpretation of the data. Furthermore, too many systems are perceived as a "black box", where physicians feel they do not have any understanding of how such systems work and how they generate their diagnoses.

Accordingly, it would be desirable and highly advantageous to have a CADx system that is an "open box", increasing its acceptance among physicians.

SUMMARY OF THE INVENTION

The problems stated above, as well as other related problems of the prior art, are solved by the present invention, an interactive computer-aided diagnosis (ICAD) method and system for assisting diagnosis of lung nodules in digital volumetric medical images.

The method and system mesh seamlessly with physicians in their current work practices. By incorporating the physicians' years of training into the present invention, the invention takes advantage of their knowledge, augmenting it with the strengths of the computer in rapid computation of numeric values. Such an invention is an "open box", increasing its acceptance among physicians. The invention provides results in "real-time" so that it does not add a time delay to the physician's examination process.

According to an aspect of the invention, there is provided a computer-assisted diagnosis method for assisting diagnosis of anatomical structures in a digital volumetric medical image of at least one lung. An anatomical structure of interest is identified in the volumetric digital medical image. The anatomical structure of interest is automatically segmented, in real-time, in a predefined volume of interest (VOI). Quantitative measurements of the anatomical structure of interest are automatically computed, in real-time. A result of the segmenting step and a result of the computing step are displayed, in real-time. A likelihood that the anatomical structure of interest corresponds to a disease or an area warranting further investigation is estimating, in real-time, based on predefined criteria and the quantitative measurements. A warning is generated, in real-time, when the likelihood is above a predefined threshold.

According to another aspect of the invention, the method further includes the step of generating a graphical user interface having a main window for displaying at least one view corresponding to the at least one lung.

According to yet another aspect of the invention, the at least one view is at least one of an axial view and a maximum intensity projection view.

According to still yet another aspect of the invention, the method further includes the step of displaying at least one of the result of the segmenting step and the result of the computing step in a supplemental window or a pop-up window of the graphical user interface.

According to a further aspect of the invention, the method further includes the step of alternately displaying at least one of at least two different sets of display parameters in a supplemental window of the graphical user interface to view an extent of calcification of the anatomical structure of interest.

According to a yet further aspect of the invention, the method further includes the step of determining a local spinning plane for the anatomical structure of interest. The local spinning plane is centered at a centroid and a local spinning axis of the anatomical structure of interest. The local spinning plane is rotated at least a portion of 360 degrees. A view is created of the anatomical structure of interest at predefined increments of rotation, so as to result in a plurality of views of the anatomical structure of interest.

The plurality of views of the anatomical structure of interest are displayed in a supplemental window of the graphical user interface.

According to an additional aspect of the invention, there is more than one anatomical structure of interest, and the method further includes the step of conducting a tour of the more than one anatomical structure of interest. The conducting step includes the steps of displaying results of the segmenting and computing steps in at least one supplemental window or at least one pop-up window of the graphical user interface, and receiving indicia for selecting a previous anatomical structure of interest, a next anatomical structure of interest, and a particular anatomical structure of interest from among the more than one anatomical structure of interest.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to an interactive computer-aided diagnosis (ICAD) method and system for assisting diagnosis of lung nodules in digital volumetric medical images.

It is to be understood that the present invention may be implemented in various forms of hardware, software, firmware, special purpose processors, or a combination thereof. Preferably, the present invention is implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present invention is programmed. Given the teachings herein, one of ordinary skill in the related art will be able to contemplate these and similar implementations or configurations of the present invention.

Figure 1:
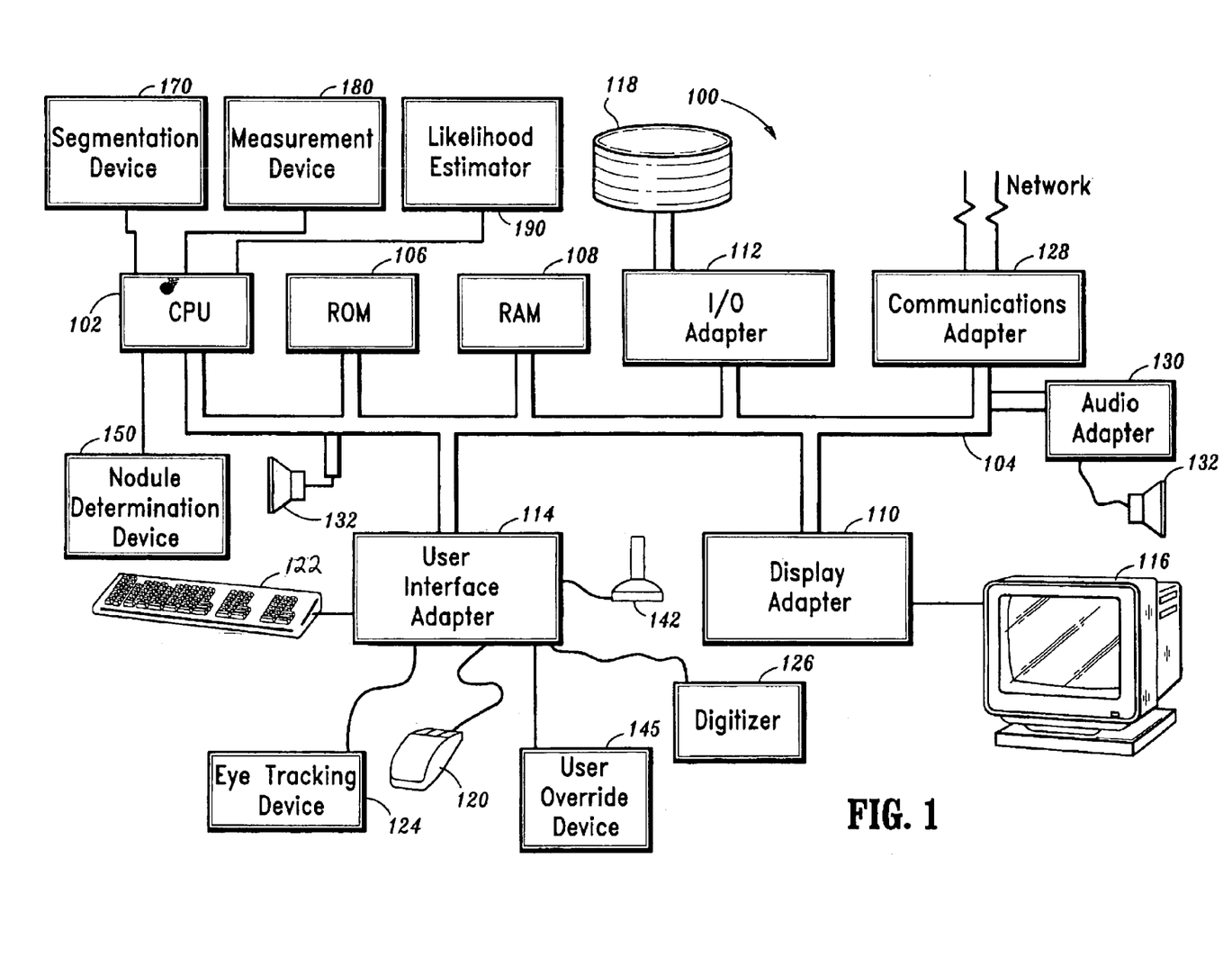
FIG. 1 is a block diagram of an interactive computer-assisted diagnosis (ICAD) system 100 for assisting diagnosis of lung nodules in digital volumetric medical images, according to an illustrative embodiment of the invention.

FIG. 1 is a block diagram of an interactive computer-assisted diagnosis (ICAD) system 100 for assisting diagnosis of lung nodules in digital volumetric medical images, according to an illustrative embodiment of the invention. The ICAD system 100 includes at least one processor (CPU) 102 operatively coupled to other components via a system bus 104. A read only memory (ROM) 106, a random access memory (RAM) 108, a display adapter 110, an I/O adapter 112, a user interface adapter 114, and an audio adapter 130 are operatively coupled to the system bus 104.

A display device 116 is operatively coupled to the system bus 104 by the display adapter 110. A disk storage device (e.g., a magnetic or optical disk storage device) 118 is operatively coupled to the system bus 104 by the I/O adapter 112.

A mouse 120, a keyboard 122, an eye tracking device 124, and a joystick 142 are operatively coupled to the system bus 104 by the user interface adapter 114. The mouse 120, keyboard 122, eye tracking device 124, and joystick 142 are used to aid in the selection of suspicious regions in a digital medical image. Any of the mouse 120, keyboard 122, eye tracking device 124, and joystick 142 may be referred to herein as a selection device. A user override device 145 is also operatively coupled to the system bus 104 by the user interface adapter 114. The user override device 145 may be a device similar to a selection device as described above, or may be any type of device which allows a user to input a user rendered decision to the system 100.

At least one speaker or other audio signal generator 132 (hereinafter "speaker" 132) is coupled to the audio adapter 130 for providing a warning or other audio information to the user. In the case when the speaker 132 is providing a warning, the speaker 132 may also be referred to herein as a "warning generator".

A nodule determination device 150, a segmentation device 170, a measurement device 180, and a likelihood estimator 190 are also included in the ICAD system 100. While the nodule determination device 150, the segmentation device 170, the measurement device 180, and the likelihood estimator 190 are illustrated as part of the at least one processor (CPU) 102, these components are preferably embodied in computer program code stored in at least one of the memories and executed by the at least one processor 102. Of course, other arrangements are possible, including embodying some or all of the computer program code in registers located on the processor chip. Given the teachings of the invention provided herein, one of ordinary skill in the related art will contemplate these and various other configurations and implementations of the nodule determination device 150, the segmentation device 170, the measurement device 180, and the likelihood estimator 190, as well as the other elements of the ICAD system 100, while maintaining the spirit and scope of the present invention.

The ICAD system 100 may also include a digitizer 126 operatively coupled to system bus 104 by user interface adapter 114 for digitizing an MRI or CT image of the lungs. Alternatively, digitizer 126 may be omitted, in which case a digital MRI or CT image may be input to ICAD system 100 from a network via a communications adapter 128 operatively coupled to system bus 104.

Figure 5:
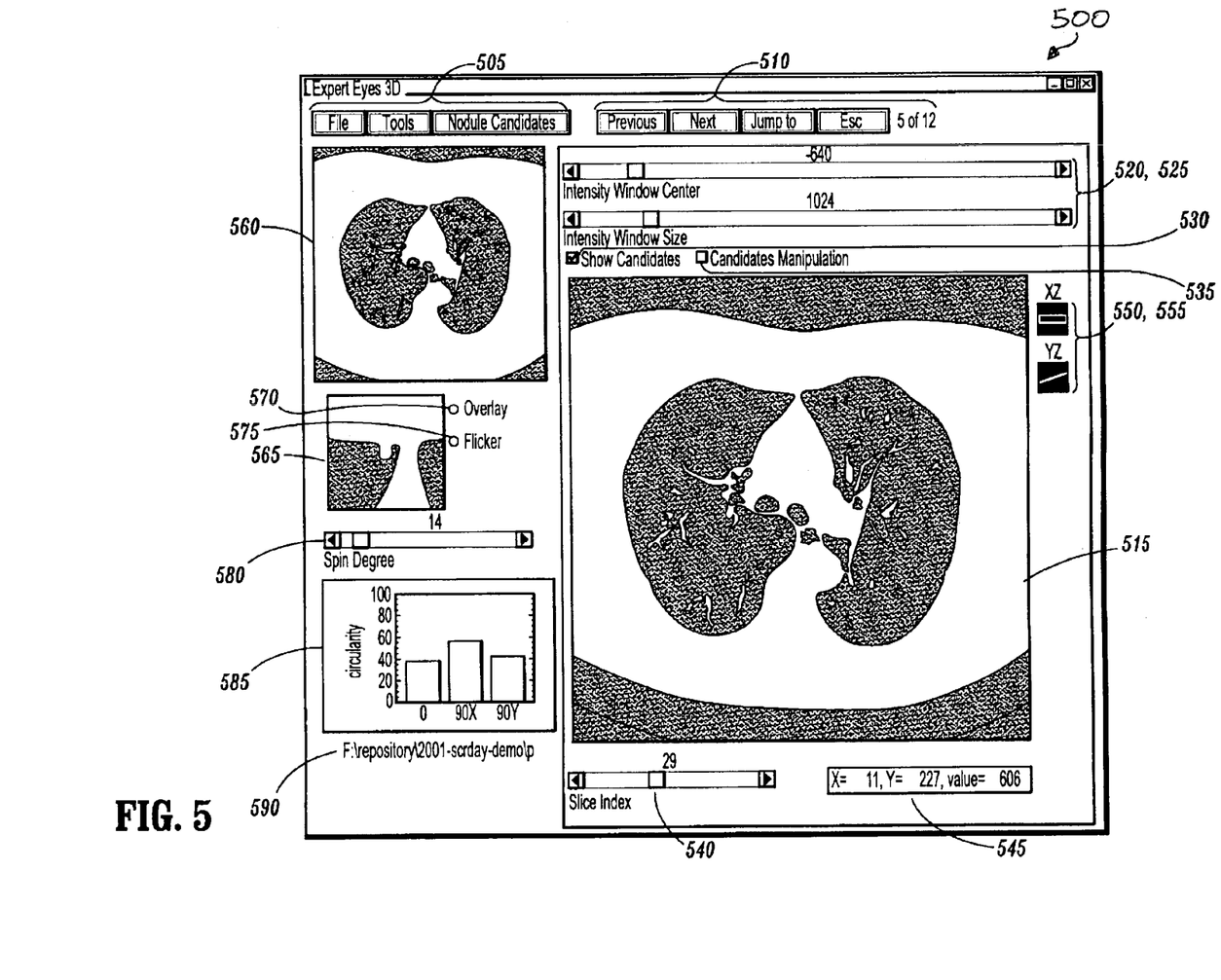
FIG. 5 is a diagram illustrating a main window of the ICAD system 100, represented by a graphical user interface, according to an illustrative embodiment of the present invention.

FIG. 5 is a diagram illustrating a main window 500 of the ICAD system 100, represented by a graphical user interface, according to an illustrative embodiment of the present invention. The main window 500 includes a main menu 505, a "Candidate Tour" menu 510, an axial image window 515, an intensity window center slider 520, an intensity window size slider 525, a show candidates selector 530, a candidates manipulation selector 535, a slice slider 540, a current position information region 545, XZ 550 and YZ 555 spinning plane illustrations (elements 520–555 correspond to the axial image window 515), a Maximum Intensity Projection (MIP) 560, a "spinning"/"flicker" window 565, an overlay selector 570, a flicker selector 575, a spinning slider 580 (elements 570–580 correspond to the "spinning"/"flicker" window 565), a circularity plot 585, and a patient information region 590.

Figure 6:
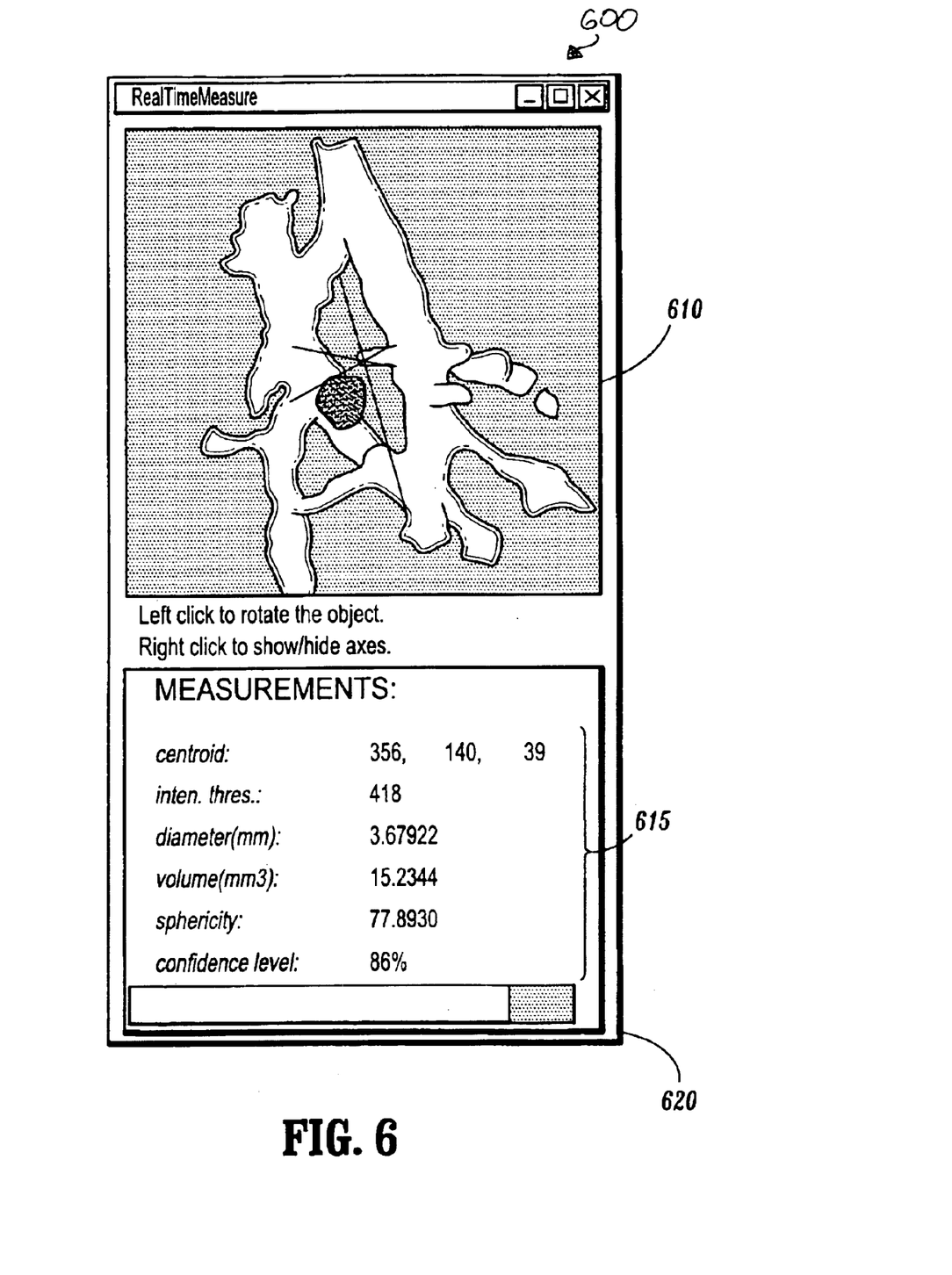
FIG. 6 is a diagram of a "pop-up" window, corresponding to the main window 500 of FIG. 5, for displaying a real-time, three-dimensional segmentation of an object of interest and quantitative measurements and a confidence level corresponding thereto, according to an illustrative embodiment of the present invention.

FIG. 6 is a diagram of a "pop-up" window 600, corresponding to the main window 500 of FIG. 5, for displaying a real-time, three-dimensional segmentation of an object of interest and quantitative measurements and a confidence level corresponding thereto, according to an illustrative embodiment of the present invention. The pop-up window 600 includes a three-dimensional rendering window 610, a quantitative measurements region 615, and a confidence level bar plot 620.

In the ICAD system 100, "candidate objects" may be automatically located by an integrated automatic detection program, or manually selected by the user. A candidate object is an anatomical structure that either the user or the computer has deemed sufficiently suspicious as to warrant further examination. Candidate objects are also referred to herein as "objects of interest", "structures of interest", or simply candidates. A "volume of interest" (VOI) is a 3D volume of the data which contains an "object of interest", although it may contain other objects as well that are not of interest. In general, the idea is to identify and classify nodules versus non-nodules.

If the automatic detection program is chosen, the user is taken on a "Candidate Tour" to sequentially examine and validate all the candidate objects detected by the computer. During a "Candidate Tour", the "Candidate Tour" menu 510 is invoked. Also, the total number of candidate objects is displayed, as well as the number of the candidate object currently being shown, with a "n of m" label 590 included in the "Candidate Tour" menu 510. The user may go to the "next" candidate, return to examine a "previous" candidate, or "jump to" a particular candidate by actuating corresponding buttons of the "Candidate Tour" menu 510. Interactive tools and automatic measurements as described herein are made available to the user for aid in validation of the automatically or manually detected candidates. While illustrative interactive tools and measurements are described herein to aid in the comprehension of the present invention, it is to be appreciated that other interactive tools and/or measurement may be employed while maintaining the spirit and scope of the present invention.

Whether the volume of interest to be examined is determined by the user or by the automatic detection method, the automatic segmentation method automatically segments any object in the lungs at that position. The object of interest may be a lung nodule, or may correspond to an airway wall, vessel, or other anatomical structure, which appears as a bright opacity in CT images. The ICAD system 100 automatically performs an adaptive threshold operation based upon automatic local histogram analysis to segment the object of interest (see the above referenced application, Ser. No. 09/840,266, entitled "Method and System for Automatically Detecting Lung Nodules from High Resolution Computed Tomography (HRCT) Images", and then measures and characterizes the object. Such measurements and characterizations are shown in the pop-up window 600 of FIG. 6.

Once the candidate object has been segmented, properties of the candidate object are measured. These measurements include, for example, the object's centroid, diameter, volume, circularity, sphericity, and average intensity, as shown in the pop-up window of FIG. 6. Anatomical knowledge is used to reason about the likelihood that the object of interest corresponds to a nodule. The CAD system 100 computes a confidence measurement indicating the CAD system's estimate of the likelihood that the object is a nodule. These measurements are described in the above referenced application, Ser. No. 09/840,266, entitled "Method and System for Automatically Detecting Lung Nodules from High Resolution Computed Tomography (HRCT) Images".

Axial slices are presented to the user in the axial image window 515. The user may scroll back and forth through the axial slices by sliding the slice slider 540. A volume of interest may be selected by moving the positioning device, such as a mouse or a joystick to navigate in the 3-D volumetric image data to a particular point in the current slice, or by invoking the "Candidate Tour". Once a volume of interest has been selected, the user may use several visualization tools to make a decision about whether or not the volume of interest is a nodule. These visualization tools include "fly-around", "flicker", "slice scrolling", and interaction with the three-dimensional surface rendering. Flicker, for example, may be enabled by the flicker selector 575.

"Fly-around" is a cine loop, which gives a quick, very natural visualization of the volume surrounding an object of interest. Each frame of the cine is a small slice of the data, taken at slightly different angles, centered at the point of interest. The cine gives an effect somewhat like flying around the object. This visualization allows the physician to very quickly discover the three-dimensional shape of the object and whether the object has any connecting vessels, without requiring any additional decisions such as segmentation thresholds or viewing angles. In a very short period of time, the user can determine whether an area can be safely dismissed from concern, or warrants further investigation as a lung nodule. Fly-around is described in the above referenced application, Ser. No. 09/606,564, entitled "Computer-Aided Diagnosis Method for Aiding Diagnosis of Three Dimensional Digital Image Data".

"Slice scrolling" lets the user move up and down in a narrow region around the suspect area to visualize the shape of an object. This action is similar to "fly-around" but instead of going around the object, the motion is more of a back-and-forth type motion.

If an area is deemed suspicious after "fly-around", another click of a button (the flicker selector 575) launches the "flicker" mode, giving a useful visualization of the calcification pattern, which is an important sign of malignancy. The system alternates between two sets of display parameters, one set optimized for lung tissue and the other set optimized for mediastinal tissue. This allows the user to see which areas of the suspicious area have been calcified and which have not been calcified.

The result of the automatic segmentation is shown in a separate window (the pop-up window 600 of FIG. 6) as a shaded surface display or a volume rendering. Significant adjacent anatomical structures, such as blood vessels and the chest wall, are also shown, giving an intuitive understanding of the shape and position of the object of interest. The segmented object is shown in one color, whereas the surrounding tissues are shown in a contrasting color. This allows the physician to see the nodule in conjunction with its surroundings, and to verify that that the system's automatic segmentation is valid.

If the object warrants further examination, the user can easily interact with the three-dimensional rendering to see the object on all sides. The measurements of the segmented object, including diameter, volume, sphericity, and so forth are instantly displayed for the user (as shown in FIG. 6). Upon a click of a button, these measurements (or a subset thereof) are stored in a table for reporting, and for comparison with earlier or subsequent measurements. In this way, the growth of nodules over time may be closely monitored.

The real-time segmentation allows the user to manipulate the selecting device as an interactive "volume probe". The physician places the device, using his or her experience and training to determine which areas merit examination. The ICAD system 100 instantaneously segments whatever object is at that position using the adaptive thresholding technique. As the object is segmented, the system measures the object and computes the confidence value. If the confidence measurement (shown in FIG. 6) indicates that the object is likely to correspond to a lung nodule, the system will generate an audible warning through speaker 132. Of course, other types of warnings may be provided, such as for example, visual warnings.

Taken together, these real-time automatic visualization and measurement techniques provide powerful interactive tools for physicians examining volumetric images of the body. The fast and natural presentation does not add a burden to the user, but instead presents useful and timely information which greatly enhances a physician's ability to make decisions about diagnosis and treatment. The nearly instantaneous segmentation and measurement of three-dimensional objects fulfills an important need for physicians. Objects of typical size can be segmented in less than 1 second on an 833 MHz PC with 1 GB of memory. Very large objects may take slightly longer. The interactive reporting of the object's characteristic measurements and the confidence value make the system an "open box" so that the user can easily understand why the automatic detection system made the decisions that it did. In this way, the ICAD system 100 will be more acceptable to users as they gain confidence in understanding how it works.

Figure 2:
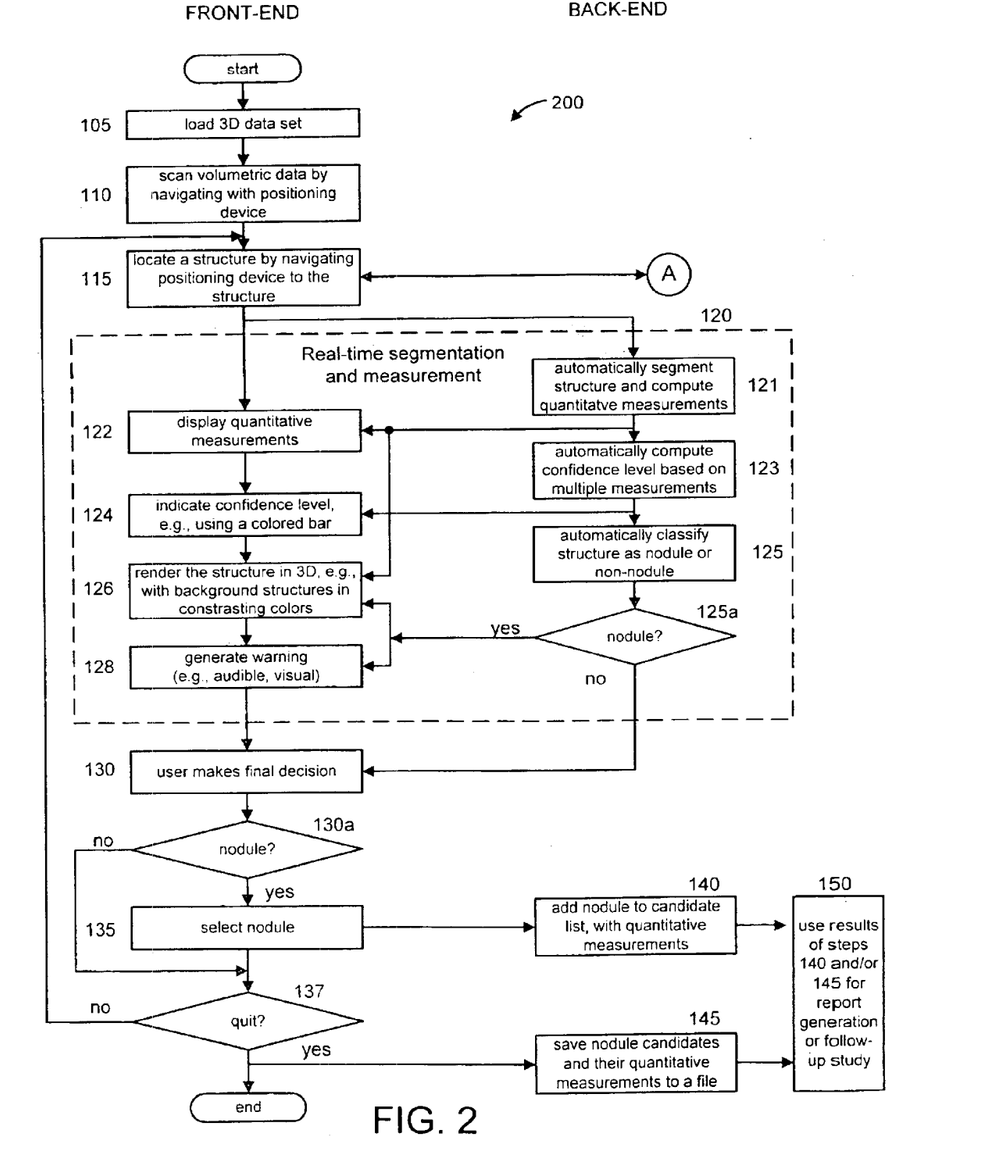
FIG. 2 is a flow diagram illustrating an interactive computer-aided diagnosis (ICAD) method 200 for assisting the detection of lung nodules in digital volumetric medical images, according to an illustrative embodiment of the present invention.

FIG. 2 is a flow diagram illustrating an interactive computer-aided diagnosis (ICAD) method 200 for assisting the detection of lung nodules in digital volumetric medical images, according to an illustrative embodiment of the present invention.

As used herein, the term "back-end" refers to a portion of either a system (ICAD system 100) or method (methods 200 and 300), wherein the portion, operations performed thereby, and/or results obtained therefrom are not visible to the user. The term "front-end" refers to a portion of either a system (ICAD system 100) or method (methods 200 and 300), wherein the portion, operations performed thereby, and/or results obtained therefrom are visible to the user. The steps depicted in FIGS. 2 and 3, which are arranged on the left side thereof, correspond to the front-end. The steps depicted in FIGS. 2 and 3, which are arranged on the right side thereof, correspond to the back-end.

Volumetric data (e.g., three-dimensional data) for a set of the lungs is loaded (step 105). A user scans the data using a selection device (step 110). Step 110 may be performed, for example, using the mouse 120 or the joystick 142 as follows: (1) click on a sliding bar (e.g., the slice slider 540) to move up and down or to jump to a certain slice; and (2) navigate the scrolling by the movement of the selection device. As is evident, the first approach shows axial slices discretely, while the second approach shows axial slices continuously. Of course, other approaches and devices may be used to scan the data, while maintaining the spirit and scope of the present invention.

The user locates/selects an anatomical structure of interest (hereinafter "structure of interest") to be examined by simply pointing to the structure of interest using the selection device (step 115). Alternatively (as indicated by reference character "A"), the user can perform the steps illustrated with respect to FIG. 3 below, if the user decides to examine previously detected structures of interest.

Continuing with the method of FIG. 2, real-time segmentation and measurements are computed in the back-end, and the results displayed in the front-end, e.g., in the pop-up window 600 of FIG. 6 (step 120). Step 120 provides quantitative measurements and intuitive display of the structure of interest.

In the back-end, the segmentation device 170 automatically segments the structure of interest based on local histogram analysis (step 121). This segmentation may be performed, for example, as described in the above referenced application, Ser. No. 09/840,266, entitled "Method and System for Automatically Detecting Lung Nodules from High Resolution Computed Tomography (HRCT) Images. Also, at step 121, measurements of the object are computed by the measurement device 180 based on a segmentation result from the segmentation device 170. These measurements include the centroid, diameter, volume, sphericitiy, average and standard deviation of intensity. The back-end communicates the results to the front-end.

The front-end receives messages from the back-end and displays measurement results (step 122). While the segmentation results and the quantitative measurements have been thus far described herein as being displayed in a pop-up window 600, other arrangements are possible which maintain the spirit and scope of the invention. For example, the segmentation results and the quantitative measurements may be displayed in the main GUI (e.g., main window 500).

In the back-end, the confidence that the anatomical structure corresponds to a lung nodule or other suspicious growth is automatically estimated by the likelihood estimator 190, based on the measurements computed at step 121 by the measurement device 180 (step 123). The confidence level is passed to the front-end at step 123.

The front-end receives the confidence level for display, e.g., in the pop-up window 600 of FIG.6 (step 124). In one illustrative embodiment of the invention, a colored bar is plotted to illustrate the confidence level. Of course, other visual enhancements may be used to display the confidence level as well as any other information provided/displayed by the front-end, while maintaining the spirit and scope of the present invention.

In the back-end, the structure of interest is automatically classified as a nodule or a non-nodule by the nodule determination device 150, based on the confidence level computed at step 123 by the likelihood estimator 190 (step 125). If the structure of interest is considered to be a nodule (step 125a), a message is sent to the front-end.

The front-end provides three-dimensional rendering, such as shaded surface rendering, volume rendering, and so forth, of the structure of interest, as well as its neighboring structures, e.g., in the pop-up window 600 of FIG. 6 (step 126). Preferably, but not necessarily, colors are used to differentiate the structure of interest from nearby structures. A user can rotate the rendering in three-dimensions as desired, to have an intuitive understanding of the shape and position of the structure.

If the front-end is informed that the structure under examination is likely to correspond to a nodule, then an audible alarm signal (e.g., a beep) is generated by speaker 132 to alert the user of the same (step 128).

The user makes the final decision to classify the structure of interest as a nodule or non-nodule, based on the provided information (measurements and three-dimensional rendering), as well as the user's visual examination of the original images (step 130). The final decision is input by the user to the user override device 145.

If the final decision is that the structure is a nodule or other structure (step 130a) that should be recorded for future reference, then the user enables the "candidate manipulation" mode and clicks on the nodule or other structure to confirm recordation (step 135). Such recordation may be with respect to, e.g., the disk storage device 118 and/or the random access memory 108.

In the back-end, the location of the nodule, along with its measurements, is automatically added to the nodule candidate list (step 140).

If user wants to quit the examination process or wants to begin a new study (step 137), then the candidate list is automatically saved to a file (step 145).

Any results recorded at steps 140 and 145 can be further used for report generation or follow-up study (step 150).

Figure 3:
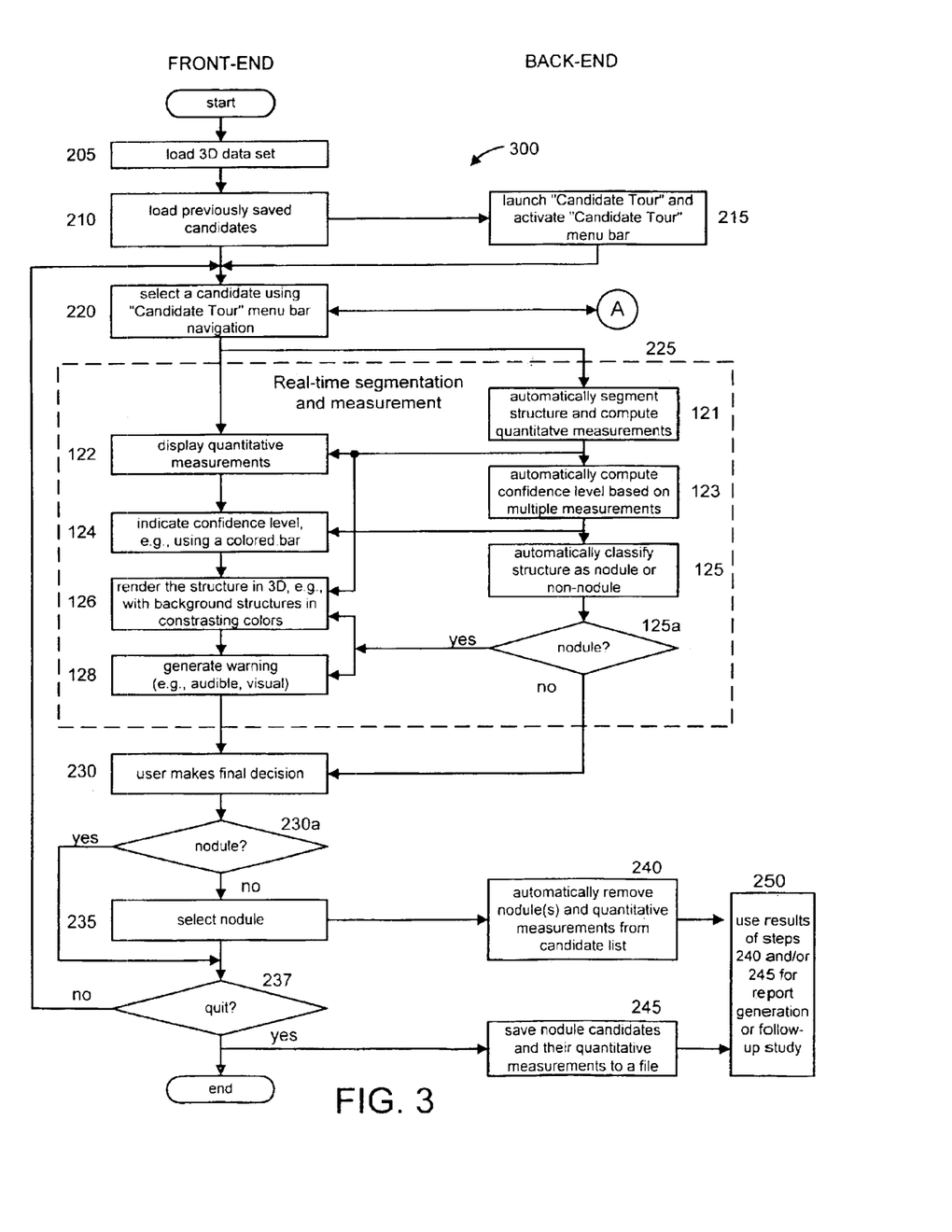
FIG. 3 is a flow diagram illustrating an interactive computer-aided diagnosis (ICAD) method 300 for assisting diagnosis of previously detected lung nodules in digital volumetric medical images, according to an illustrative embodiment of the present invention.

FIG. 3 is a flow diagram illustrating an interactive computer-aided diagnosis (ICAD) method 300 for assisting diagnosis of previously detected lung nodules in digital volumetric medical images, according to an illustrative embodiment of the present invention.

Volumetric data (e.g., three-dimensional data) for a set of the lungs is loaded (step 205). Previously saved candidate objects are loaded (step 210). These candidate objects can be obtained, for example, using two illustrative approaches: (1) manual detection, where the user examines the data and manually picks out the candidate objects as described in FIG. 2; and (2) automatic detection, wherein the computer detects candidate objects within the entire lung volume. The second approach may be implemented, for example, using a method such as the one described in the above referenced application, Ser. No. 09/840,266, entitled "Method and System for Automatically Detecting Lung Nodules from High Resolution Computed Tomography (HRCT) Image".

In the back-end, the computer launches a "Candidate Tour", which activates the "Candidate Tour" menu 510 (step 215). The "Candidate Tour" is a function that automatically navigates the user to each of the candidate objects for examination and confirmation. All the interactive measurement and display functions shown in steps 122–128 of FIG. 2 are accessible to the user. The "Candidate Tour" menu bar 510 provides functions that enable the user to select candidates easily, such as "Previous", "Next", and "Jump to".

The user selects a candidate object to examine using the "Candidate Tour" menu bar (step 220). Alternatively (as indicated by reference character "A"), the user can perform the steps illustrated with respect to FIG. 2, if the user decides to examine new candidate objects.

Real-time segmentation and measurement is launched (via segmentation device 170 and measurement device 180) to provide the user quantitative measurements and intuitive displaying of the structure of interest, e.g., as shown in the pop-up window 600 of FIG. 6, via the display device 116 (step 225). Step 225 is described in further detail with respect to step 120 of FIG. 2.

The user makes the final decision to classify the structure of interest as a nodule or a non-nodule, based on the provided measurements and three-dimensional rendering, as well as the user's manual study of the original images (step 230). The final decision is input by the user to the user override device 145. This step is identical to step 130 of FIG. 2.

If the final decision considers the structure as a non-nodule (step 230a), then the user enables the "candidate manipulation" mode and clicks on the structure (or an index or visual mark corresponding thereto) to discard the structure from the list (step 235).

In the back-end, the non-nodule and the quantitative measurements for the non-nodule are automatically removed from the candidate list (step 240).

If user wants to quit the re-examination process or wants to begin a new study (step 237), then the candidate list is automatically saved to a file (step 245). This step is identical to step 145 of FIG. 2.

Any results recorded at steps 240 and 245 can be further used for report generation or follow-up study (step 250). This step is identical to step 150 of FIG. 2.

Figure 4:
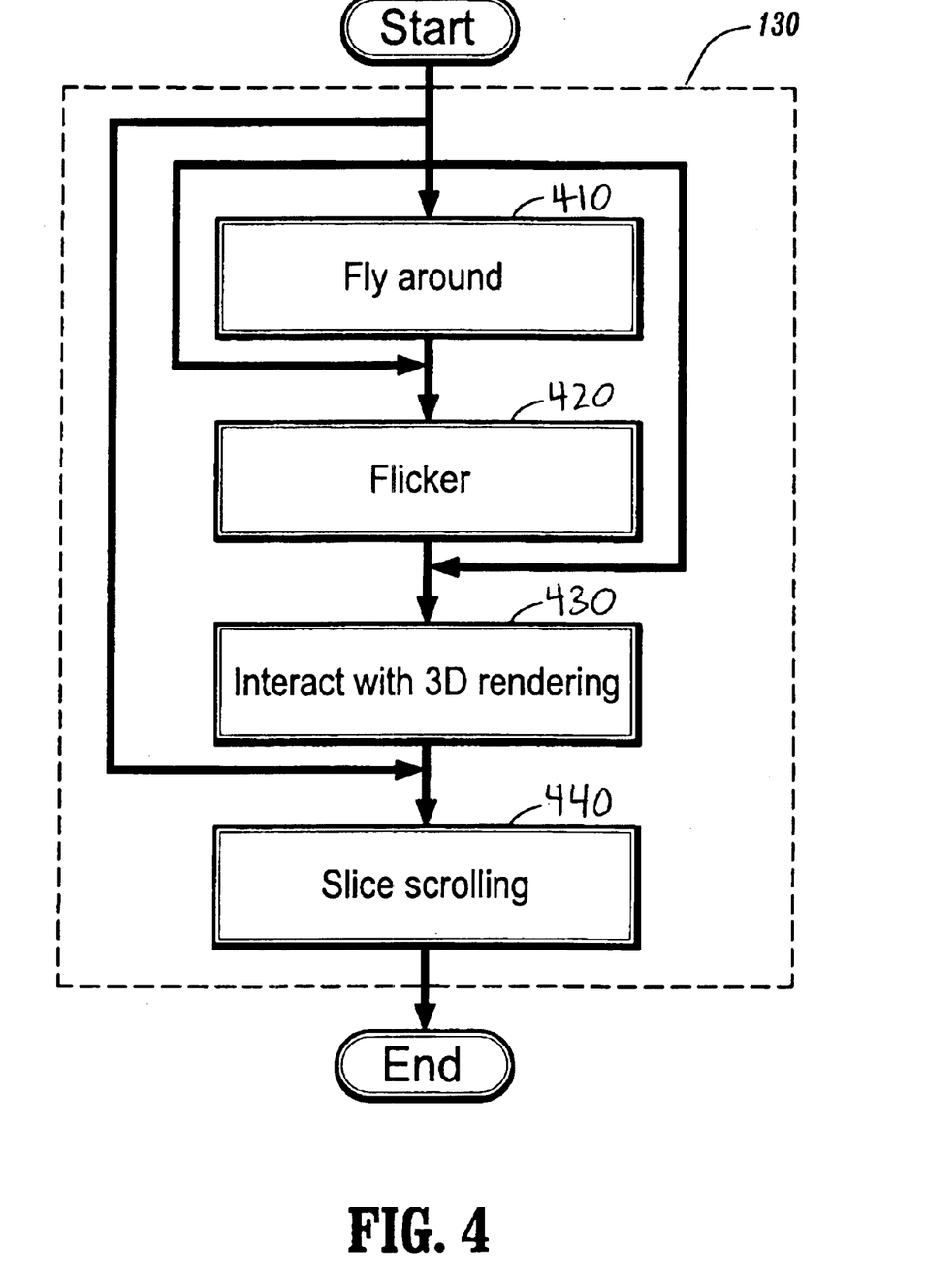
FIG. 4 is a diagram illustrating visualization tools used for supporting user decisions with respect to the methods of FIGS. 2 and 3, according to an illustrative embodiment of the present invention.

FIG. 4 is a diagram illustrating visualization tools used for supporting user decisions with respect to the methods of FIGS. 2 and 3, according to an illustrative embodiment of the present invention. It is to be appreciated that the user may select one or more of the visualization tools.

The user selects "Fly Around" to view a short movie of two-dimensional slices of the nodule (step 410). The user may select individual frames of the movie by means of the spinning slider described above.

The user selects "Flicker" to have the computer alternate between two sets of display parameters, to view the extent of calcification of a candidate object (step 420).

The user interacts with a three-dimensional rendering of a candidate object (shown in step 126 of FIG. 2) by means of the mouse 120, the joystick 142, and so forth, to view different sides of the candidate object (step 430).

The user scrolls up and down within slices adjacent to a candidate object (slice scrolling) (step 440).

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A computer-assisted diagnosis method for assisting diagnosis of anatomical structures in a digital volumetric medical image of at least one lung, comprising the steps of:
   identifying an anatomical structure of interest in the volumetric digital medical image;
   automatically segmenting, in real-time, the anatomical structure of interest in a predefined volume of interest (VOI);
   automatically computing, in real-time, quantitative measurements of the anatomical structure of interest, and executing a segmentation method that adaptively adjusts a segmentation threshold based on a local histogram analysis to determine an extent of the structural object of interest;
   displaying, in real-time, a result of said segmenting step and a result of said computing step;
   estimating, in real-time, a likelihood that the anatomical structure of interest corresponds to a disease or an area warranting further investigation, based on predefined criteria and the quantitative measurements;
   generating, in real-time, a warning, when the likelihood is above a predefined threshold; and
   generating a graphical user interface having a first window for displaying at least one view of the at least one lung, and a second window for displaying at least one of the result of said segmenting step and the result of said computing step.

2. The method according to claim 1, wherein said generating step comprises the step of rendering a visual confidence bar.

3. The method according to claim 1, wherein said generating step comprises the step of creating an audible signal.

4. The method according to claim 1, wherein said displaying step comprises the step of rendering a colored, three-dimensional representation of the anatomical structure of interest, with background structures, if any, rendered in contrasting colors with respect to the anatomical structure of interest.

5. The method according to claim 1, wherein the quantitative measurements comprise at least one of a diameter, a volume, a sphericity, a circularity, and an average intensity of the anatomical structure of interest.

6. The method according to claim 1, wherein said identifying step is performed manually by a user.

7. The method according to claim 1, wherein said identifying step is performed automatically.

8. The method according to claim 1, wherein there is more than one anatomical structure of interest, and said method further comprises the step of repeating said segmenting, displaying, estimating, and generating steps, to examine each of the more than one anatomical structure of interest one of sequentially and randomly.

9. The method according to claim 8, wherein the more than one anatomical structure of interest is displayed with an n of m label, n representing a currently examined anatomical structure of interest and m representing a total number of the more than one anatomical structure of interest.

10. The method according to claim 1, wherein said segmenting and computing steps are performed substantially instantaneously.

11. The method according to claim 1, wherein the at least one view is at least one of an axial view and a maximum intensity projection view.

12. The method according to claim 1, further comprising the step of alternately displaying at least one of at least two different sets of display parameters in the second window of the graphical user interface to view an extent of calcification of the anatomical structure of interest.

13. The method according to claim 1, further comprising the steps of:
   determining a local spinning plane for the anatomical structure of interest, the local spinning plane being centered at a centroid and a local spinning axis of the anatomical structure of interest;
   rotating the local spinning plane at least a portion of 360 degrees;
   creating a view of the anatomical structure of interest at predefined increments of rotation, so as to result in a plurality of views of the anatomical structure of interest; and
   displaying the plurality of views of the anatomical structure of interest in the second window of the graphical user interface.

14. The method according to claim 1, wherein there is more than one anatomical structure of interest, and said method further comprises the step of conducting a tour of the more than one anatomical structure of interest, said conducting step comprising the steps of:
   displaying results of said segmenting and computing steps in the second window of the graphical user interface; and
   receiving indicia for selecting a previous anatomical structure of interest, a next anatomical structure of interest, and a particular anatomical structure of interest from among the more than one anatomical structure of interest.

15. An interactive computer-aided diagnosis system for assisting detection and diagnosis of lung nodules in a digital volumetric medical image of at least one lung, comprising:
   a selection device for identifying an anatomical structure of interest in the volumetric digital medical image;
   a segmentation device for automatically segmenting, in real-time, the anatomical structure of interest in a predefined volume of interest (VOI),
   a measurement device for computing, in real-time, quantitative measurements of the anatomical structure of interest, and executing a segmentation method that adaptively adjusts a segmentation threshold based on a local histogram analysis to determine an extent of the structural object of interest;
   a display device for displaying, in real-time, a result of said segmentation device and a result of said measurement device and for generating a graphical user interface having a first window for displaying at least one view of the at least one lung, and a second window for displaying at least one of the result of said segmenting step and the result of said computing step;
   a likelihood estimator for estimating, in real-time, a likelihood that the anatomical structure of interest corresponds to a disease or an area warranting further investigation, based on predefined criteria and the quantitative measurements; and
   a warning generator for generating, in real-time, a warning, when the likelihood is above a predefined threshold.

16. The system according to claim 15, wherein said display device displays a visual confidence bar in response to the warning generated by said warning generator.

17. The system according to claim 15, further comprising an audio signal generator for generating an audible signal in response to the warning generated by said warning generator.

18. The system according to claim 15, wherein said display device, in response to the warning generated by said warning generator, generates a colored, three-dimensional representation of the anatomical structure of interest, with background structures, if any, rendered in contrasting colors with respect to the anatomical structure of interest.

19. The system according to claim 15, wherein said display device displays various views of the anatomical structure of interest using the graphical user interface.

20. The system according to claim 15, wherein said segmenting device and computing device respectively segment the anatomical structure of interest and compute the quantitative measurements of the anatomical structure of interest substantially instantaneously.

21. The system according to claim 15, wherein the at least one view is at least one of an axial view and a maximum intensity projection view.

22. The system according to claim 15, wherein said display device alternately displays at least one of at least two different sets of display parameters in the second window of the graphical user interface to view an extent of calcification of the anatomical structure of interest.

23. The system according to claim 15, wherein the graphical user interface comprises a menu for selecting a previous anatomical structure of interest, a next anatomical structure of interest, and a particular anatomical structure of interest from among more than one anatomical structure of interest identified either automatically or manually.

24. The system according to claim 15, further comprising a storage device, wherein the graphical user interface comprises a menu for retrieving previously stored structures of interest from said storage device and for saving newly identified structures of interest from said storage device.

25. The system according to claim 15, wherein the graphical user interface further comprises a selector for removing one of an index and a visual mark of a current anatomical structure of interest and any quantitative measurements corresponding thereto from a list corresponding to previously stored anatomical structures of interest.

26. The system according to claim 15, further comprising a nodule determination device for determining whether the anatomical structure of interest is a lung nodule, based on the likelihood.

27. The system according to claim 15, further comprising a user override device, for overriding a result of said nodule determination device.

28. The system according to claim 15, wherein the graphical user interface comprises at least one visualization tool for application to the anatomical structure of interest.

29. A computer-assisted diagnosis method for assisting diagnosis of anatomical structures in a digital volumetric medical image of at least one lung, comprising the steps of:

receiving, in real-time, indicia indicating a position of interest within a volume of interest (VOI) of the digital volumetric medical image;

automatically segmenting, in real-time, an anatomical structure of interest in the VOI corresponding to the position;

automatically computing, in real-time, quantitative measurements of the anatomical structure of interest;

displaying, in real-time, a result of said segmenting step and a result of said computing step;

estimating, in real-time, a likelihood, when the anatomical structure of interest is potentially adverse, based on predefined criteria and the quantitative measurements;

generating, in real-time, a warning, when the likelihood is potentially adverse; and generating a graphical user interface having a first window for displaying at least one view of the at least one lung, and a second window for displaying at least one of the result of said segmenting step and the result of said computing step.

* * * * *